United States Patent
Durrant et al.

(10) Patent No.: US 9,662,035 B2
(45) Date of Patent: May 30, 2017

(54) STEADY STATE MEASUREMENT AND ANALYSIS APPROACH TO PROFILING AUDITORY EVOKED POTENTIALS FROM SHORT-LATENCY TO LONG LATENCY

(75) Inventors: John David Durrant, Allison Park, PA (US); Abreena Iris Tlumak, North Versailles, PA (US); Rafael E. Delgado, Coral Gables, FL (US); John Robert Boston, Wexford, PA (US)

(73) Assignees: Intelligent Hearing Systems, Miami, FL (US); University of Pittsburgh—of the Commonwealth System of Higher Education, Pittsburgh, PA (US)

( * ) Notice: Subject to any disclaimer, the term of this patent is extended or adjusted under 35 U.S.C. 154(b) by 141 days.

(21) Appl. No.: 13/307,212

(22) Filed: Nov. 30, 2011

(65) Prior Publication Data

US 2012/0157877 A1 Jun. 21, 2012

Related U.S. Application Data

(63) Continuation of application No. PCT/US2010/037312, filed on Jun. 10, 2010.

(51) Int. Cl.
*A61B 5/00* (2006.01)
*A61B 5/0484* (2006.01)
*A61B 5/048* (2006.01)

(52) U.S. Cl.
CPC .......... *A61B 5/04845* (2013.01); *A61B 5/048* (2013.01); *A61B 5/4064* (2013.01)

(58) Field of Classification Search
CPC .......................... A61B 5/04845; A61B 5/048

USPC ......................................................... 600/559
See application file for complete search history.

(56) References Cited

U.S. PATENT DOCUMENTS

| | | | |
|---|---|---|---|
| 5,023,783 A * | 6/1991 | Cohen et al. | 600/559 |
| 5,230,344 A | 7/1993 | Ozdamar et al. | |
| 6,071,246 A * | 6/2000 | Sturzebecher et al. | 600/559 |
| 6,974,421 B1 * | 12/2005 | Causevic et al. | 600/561 |
| 7,006,863 B2 * | 2/2006 | Maddess et al. | 600/559 |
| 7,123,955 B1 | 10/2006 | Gao et al. | |
| 2002/0117176 A1 | 8/2002 | Mantzaridis et al. | |

(Continued)

OTHER PUBLICATIONS

International Search Report and Written Opinion for PCT/US10/037312, dated Jan. 11, 2011.

*Primary Examiner* — Michael C Stout
*Assistant Examiner* — Nicholas E Kolderman
(74) *Attorney, Agent, or Firm* — Baker Botts, L.L.P.

(57) ABSTRACT

The present invention relates to methods and systems for profiling evoked potentials in brain electrical activity which apply steady state response concepts to analysis of longer latency responses reflective of activity of brain regions beyond the brainstem, up to an including the cortex. The use of repeated stimuli within a single analysis window produces a quasi steady-state response and permits a high-resolution spectral analysis. Response amplitudes were measured at repetition rates from 80 to below 1 Hz, using trains of repeated tone-burst stimuli. An amplitude measure introduced and defined as the harmonic sum was incorporated into the spectral power of the response carried by both the fundamental frequency, and the harmonics thereof. Additionally, time ensemble averaging can be employed to improve signal to noise ratio.

18 Claims, 11 Drawing Sheets

(56) References Cited

U.S. PATENT DOCUMENTS

2006/0161075 A1* 7/2006 Kurtz .......................... 600/559
2007/0032737 A1   2/2007 Causevic et al.

* cited by examiner

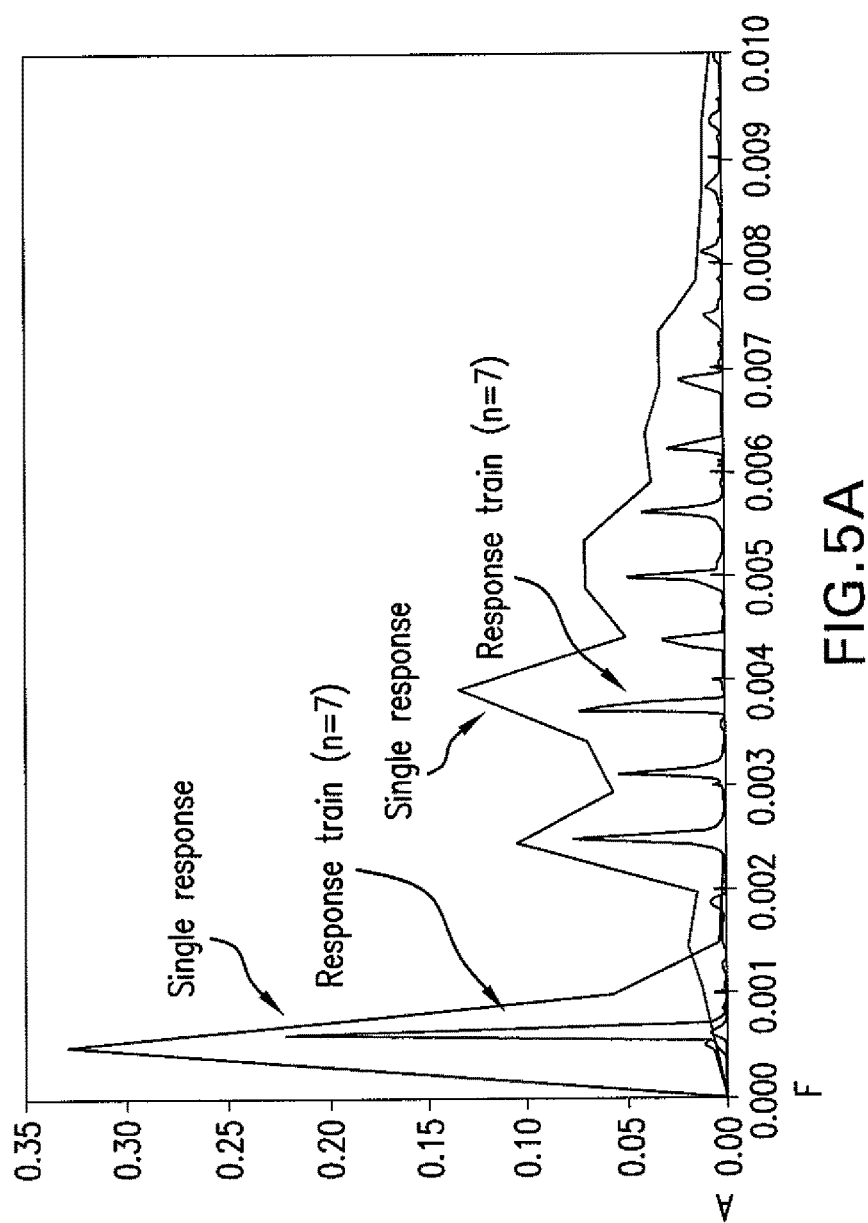

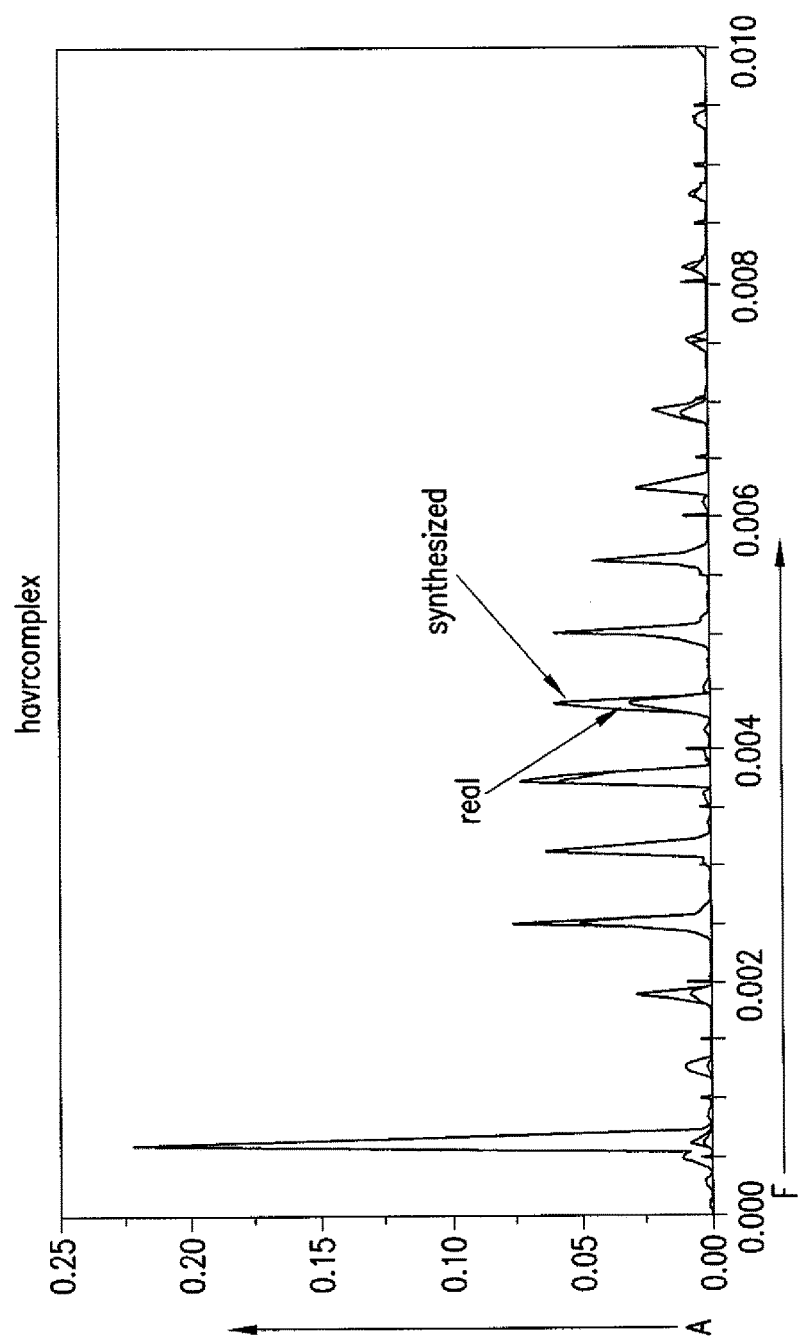

STEADY STATE MEASUREMENT AND ANALYSIS APPROACH TO PROFILING AUDITORY EVOKED POTENTIALS FROM SHORT-LATENCY TO LONG LATENCY

CROSS REFERENCE TO RELATED APPLICATIONS

The present application is a continuation of International Patent Application No. PCT/US2010/037312, filed Jun. 10, 2010, published in English on Dec. 9, 2010 as WO10/141764, and claims priority to U.S. Provisional Application Ser. No. 61/183,826, filed Jun. 3, 2009, the contents of which are hereby incorporated by reference in their entireties.

1. INTRODUCTION

The present invention relates to auditory evoked potentials which serve to assess central nervous system function by evaluating peripheral and central auditory function, and which provide a global view of the integrity of the auditory pathway. Particularly, the present invention provides a method to profile auditory steady-state response amplitudes over a wide range of stimulus repetition rates (or modulation frequencies), including those that were expected to represent the general ranges of traditional transient (obligatory) auditory evoked potentials. Additionally, the present invention utilizes the harmonic structure of the response to provide a more comprehensive analysis.

2. BACKGROUND OF THE INVENTION

The brain is well-known to be highly electrically active at all times, as evidenced by measurements on a subject's scalp in an electroencephalogram reading. This electrical activity can be synchronized with an event such as the occurrence of a discrete sound, as well as more elaborate stimuli such as a semantic change in a spoken phrase. This synchronization can be defined as an evoked potential, or evoked response, and recorded from the nervous system of a subject as an electrical potential following presentation of a stimulus. These evoked potentials are distinct from spontaneous potentials as detected by electroencephalography or electromyography.

Traditionally, transient response stimulus and analysis methods are employed to analyze auditory evoked potentials and provide a tool by which to monitor peripheral and central auditory function, assess its maturation, and overall obtain a global view of the integrity of the auditory pathway. However, there is a fundamental shortcoming of this conventional approach by virtue of the way the auditory evoked potentials are traditionally analyzed.

Conventional transient auditory evoked potentials are analyzed via signal averaging, which is performed in an effort to improve the signal-to-noise measurement embodied in a given response. However, the stimulus-related portion of the response is only known in general form from the examiner's subjective reference. Even after substantial signal-to-noise improvement, the putative response must be judged in a background of residual noise from which it can be difficult to distinguish some, if not all, of the component waves which make up the auditory evoked potential. In short, transient evoked potentials do not allow for the evoked response to be predicted, with a sufficient degree of accuracy, by the stimulus administered. Consequently, auditory evoked potential response analysis can be strongly based on examiner judgment, thus introducing the element of subjectivity to any analysis and conclusions drawn.

Furthermore, a particular challenge for researchers and clinicians alike are the potential ambiguities of wave identification over the course of maturation. In other words, the time it takes for transient auditory evoked potentials to reach well-defined adult waveforms is dependent upon structural and functional development, maturational effects of myelination, synaptic density and neuro-plasticity of the neural pathways specific to individual auditory evoked potential components. For lower sites along the auditory pathway (i.e., namely pontine-ward) development is relatively short, for example, the auditory brainstem response reach maturity by approximately two years of age. Conversely, for higher sites along the auditory pathway (i.e., namely cortical-ward) development is relatively long (which reflect middle latency response) and reach maturity by 12 years of age. Similarly, late-cortical components (which reflect long latency response) reach maturity by 17 years of age. Of particular concern is the potentially confounding maturational and pathological changes present in auditory evoked potentials, and thus potential hazards of using age-corrected norms. Moreover, even in adults, pathological changes via central nervous system disorders and trauma differentially affect auditory evoked potentials further, if not confound precise wave identification, especially with the diversity of focal injuries that can occur.

Accordingly, there is a need for a shift toward a more analytical approach to the auditory evoked response, such as the steady-state response provided in the present invention. Additionally, such an approach can further provide an alternative view of the brain's responses to auditory stimulation and can serve such interests as tracking maturational changes and/or effects of brain disease or injury, when extended to incorporate a more comprehensive representation of the auditory evoked potential component waves, namely to cover the latency range of traditional auditory evoked potentials accessed via a transient stimulus-response analysis.

3. SUMMARY OF THE INVENTION

The purpose and advantages of the present invention will be set forth in and apparent from the description that follows, as well as will be learned by practice of the present invention. Additional advantages of the present invention will be realized and attained by the methods and systems particularly pointed out in the written description and claims hereof, as well as from the appended drawings.

To achieve these and other advantages and in accordance with the purpose of the present invention, as embodied and broadly described, the present invention provides techniques for evaluating auditory steady state responses. An exemplary method includes administering an auditory stimulus to a subject over a comprehensive range of predetermined repetition rates (or modulation frequencies), with the auditory stimulus generating an electrical activity in the subject; synchronizing the electrical activity in the subject with the auditory stimulus to define an auditory evoked potential; monitoring the auditory evoked potential; identifying a plurality of spectral components of the auditory evoked potential; calculating the harmonic sum of the plurality of spectral components; determining the combined or overall magnitude of the auditory evoked potential, wherein the overall amplitude includes the plurality of spectral components.

In accordance with another aspect of the present invention the overall amplitude includes a fundamental frequency of the stimulus. Furthermore, another feature of the present invention is the identification of the fundamental and measurable harmonics to calculate a harmonic sum which includes the square root of the sum of squares of select spectral components, wherein the select spectral components have a magnitude which is greater than an estimated noise value. In some embodiments, the stimulus is administered at rates of less than about 10 Hz, for example, less than about 1 Hz. The stimulus can be administered at a progressively decreasing rate from about 80 Hz to about 0.75 Hz. Additionally, the stimulus can be a sinusoidal pulse administered at about 70 decibels to subjects that are awake or in a condition of light sleep. Further, the subjects can be adults of at least 18 years of age, or children less than 9 years of age. In accordance with another aspect of the invention the auditory evoked potential in the subject reflects the cortical activity of the brain.

Additionally, the present invention includes a system for evaluating evoked potentials in brain electrical activity using auditory steady state profiling comprising a device for administering an auditory stimulus to a subject over a range of frequencies from about 80 Hz to about 0.75 Hz, the auditory stimulus generating an auditory evoked potential in the subject indicative of the cortical activity of the brain; a sensor for detecting the auditory evoked potential; a processor for identifying a plurality of spectral components of the auditory evoked potential, the processor configured to calculate the harmonic sum of the plurality of spectral components; and an output for displaying the overall amplitude of the auditory evoked potentials, wherein the overall magnitude includes the plurality of spectral components. The harmonic sum can include the square root of the sum of squares of select spectral components, wherein the select spectral components have a magnitude which is greater than an estimated noise value, and the overall amplitude includes a fundamental frequency of the stimulus.

It is to be understood that both the foregoing general description and the following detailed description are exemplary and are intended to provide further explanation of the present invention. The accompanying drawings, which are incorporated in and constitute part of this specification, are included to illustrate and provide a further understanding of the method and system of the present invention. Together with the description, the drawings serve to explain the principles of the present invention.

4. BRIEF DESCRIPTION OF THE DRAWINGS

FIG. 5A-B are a graphical representations illustrating spectral analysis of an auditory evoked potential in accordance with the present invention.

Figure 6:
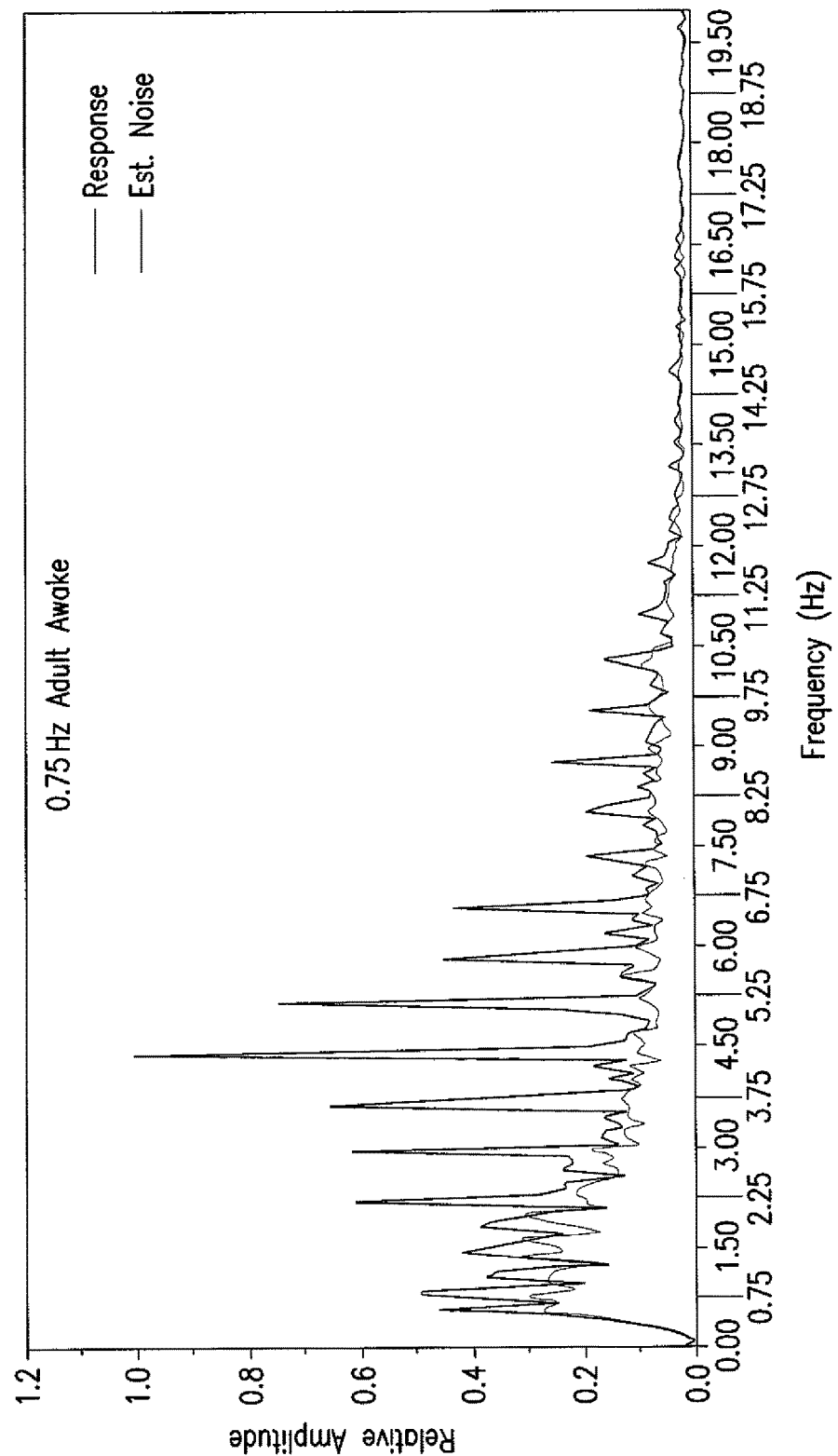

FIG. 6 is a graphical representation of an auditory evoked potential amplitude spectrum and noise floor in accordance with the present invention.

Figure 7A:
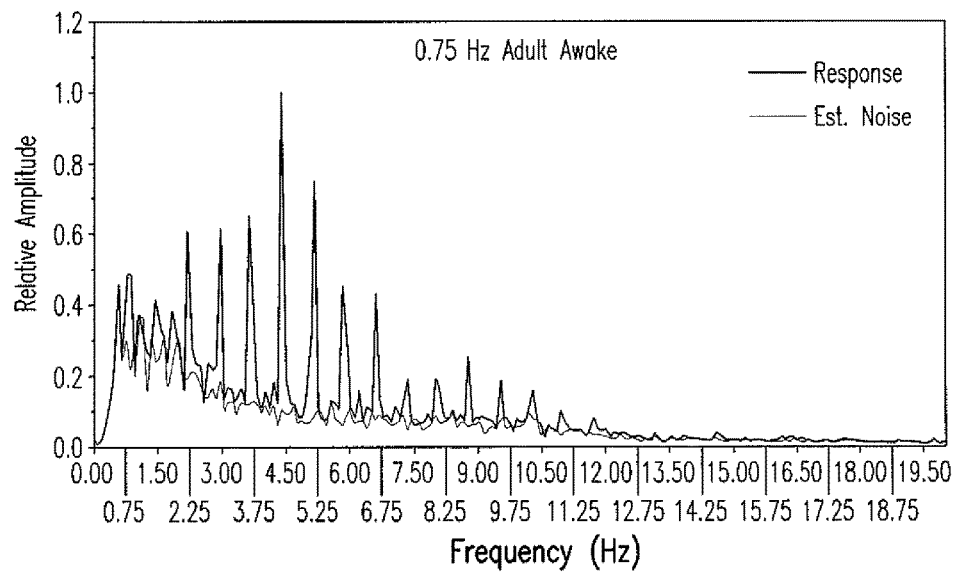
Figure 7B:
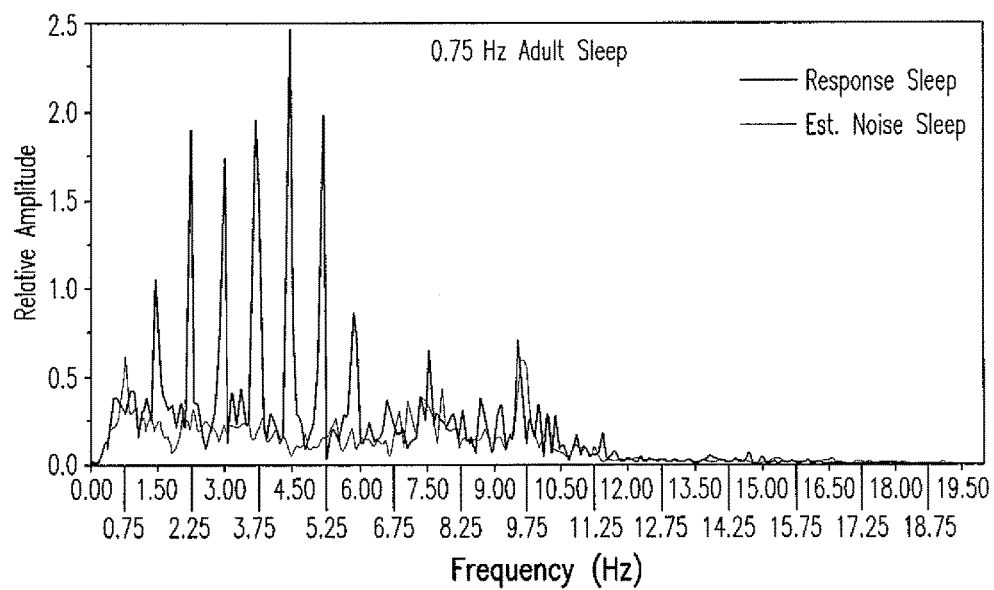

FIGS. 7A-B are a graphical representations of an auditory evoked potential amplitude spectrum of awake subjects and subjects in a state of light-sleep in accordance with the present invention.

Figure 8A:
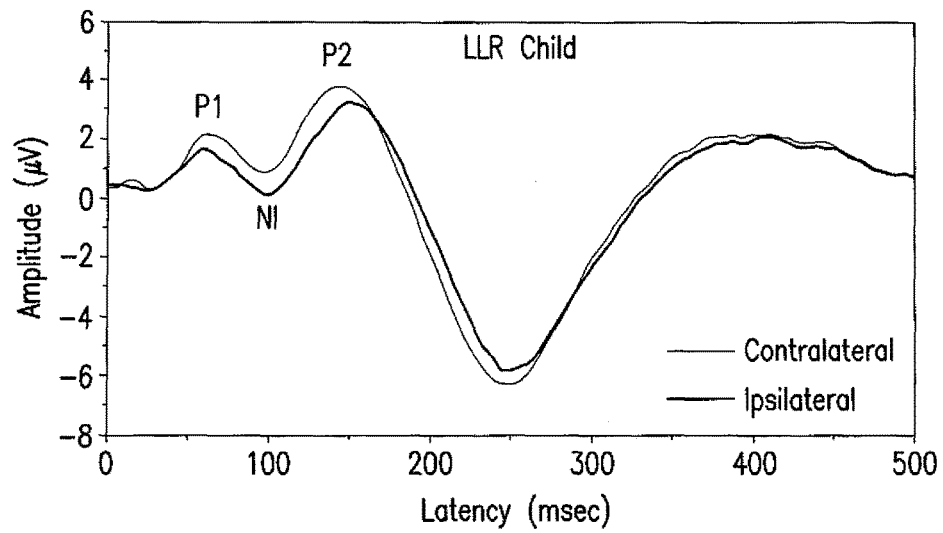
Figure 8B:
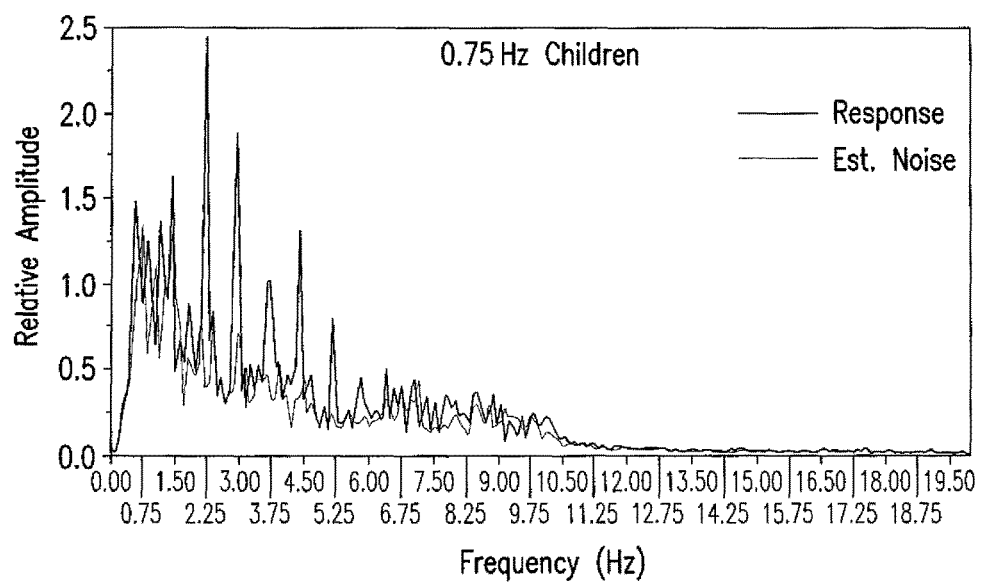

FIGS. 8A-B are a graphical representations of auditory evoked potentials in children for a transient response and an amplitude spectrum in accordance with the present invention.

Figure 9:
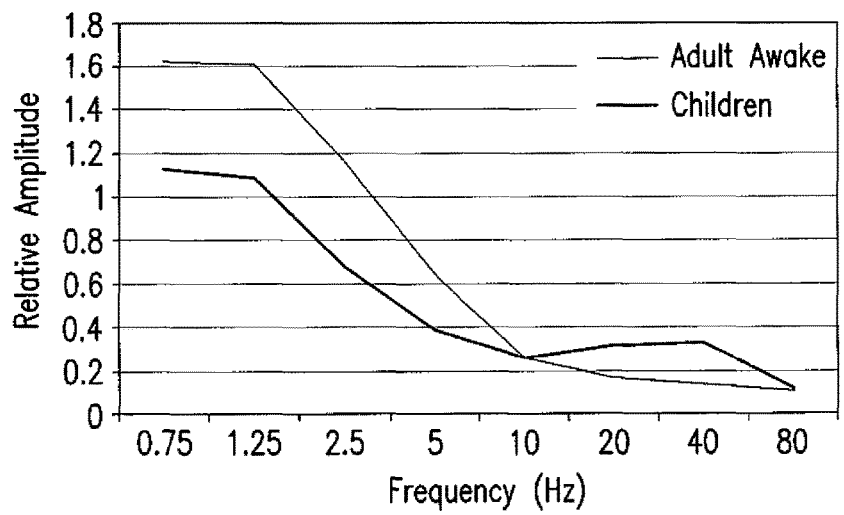

FIG. 9 is a graphical representation of auditory evoked potential profiles for children and adults in accordance with the present invention.

Figure 10:
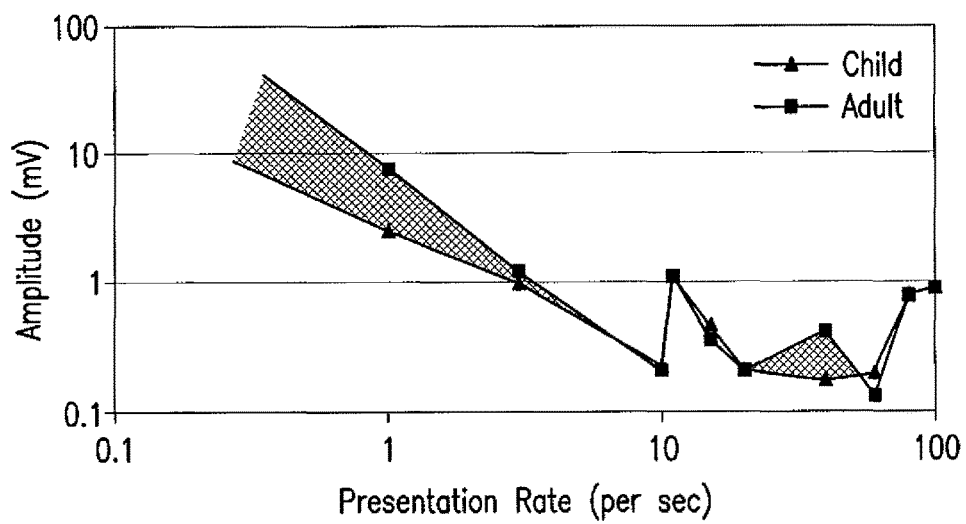

FIG. 10 is a graphical representation of transient auditory evoked potential profiles for children and adults in accordance with the present invention.

Figure 11:
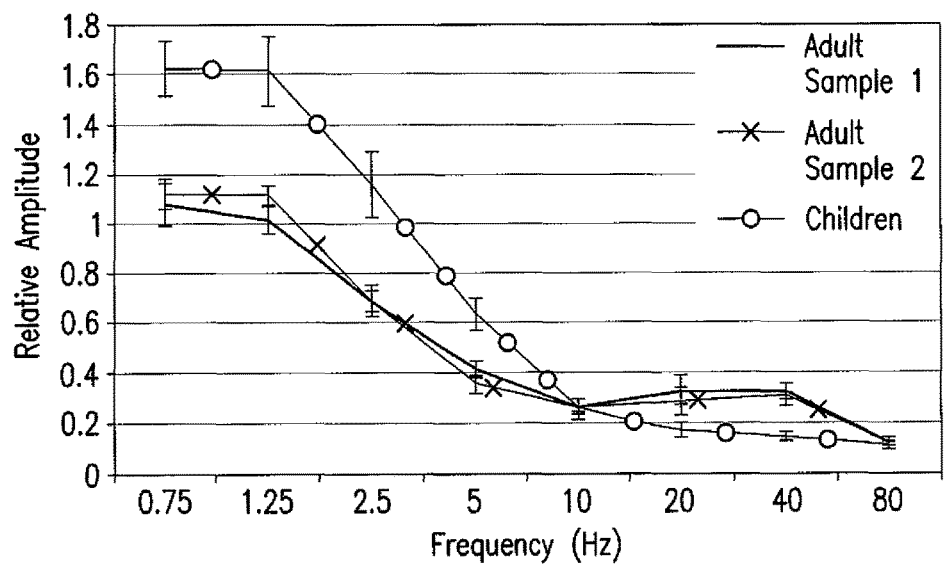

FIG. 11 is a graphical representation of auditory evoked potential profiles for children and split-half adults, including standard error bars, in accordance with the present invention.

Figure 12:
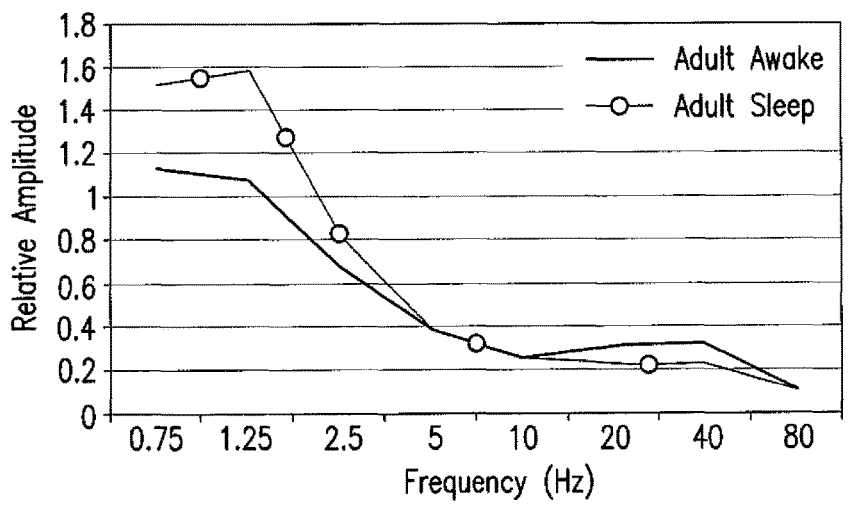

FIG. 12 is a graphical representation of an auditory evoked potential profile of awake subjects and subjects in a state of light-sleep in accordance with the present invention.

Figure 13:
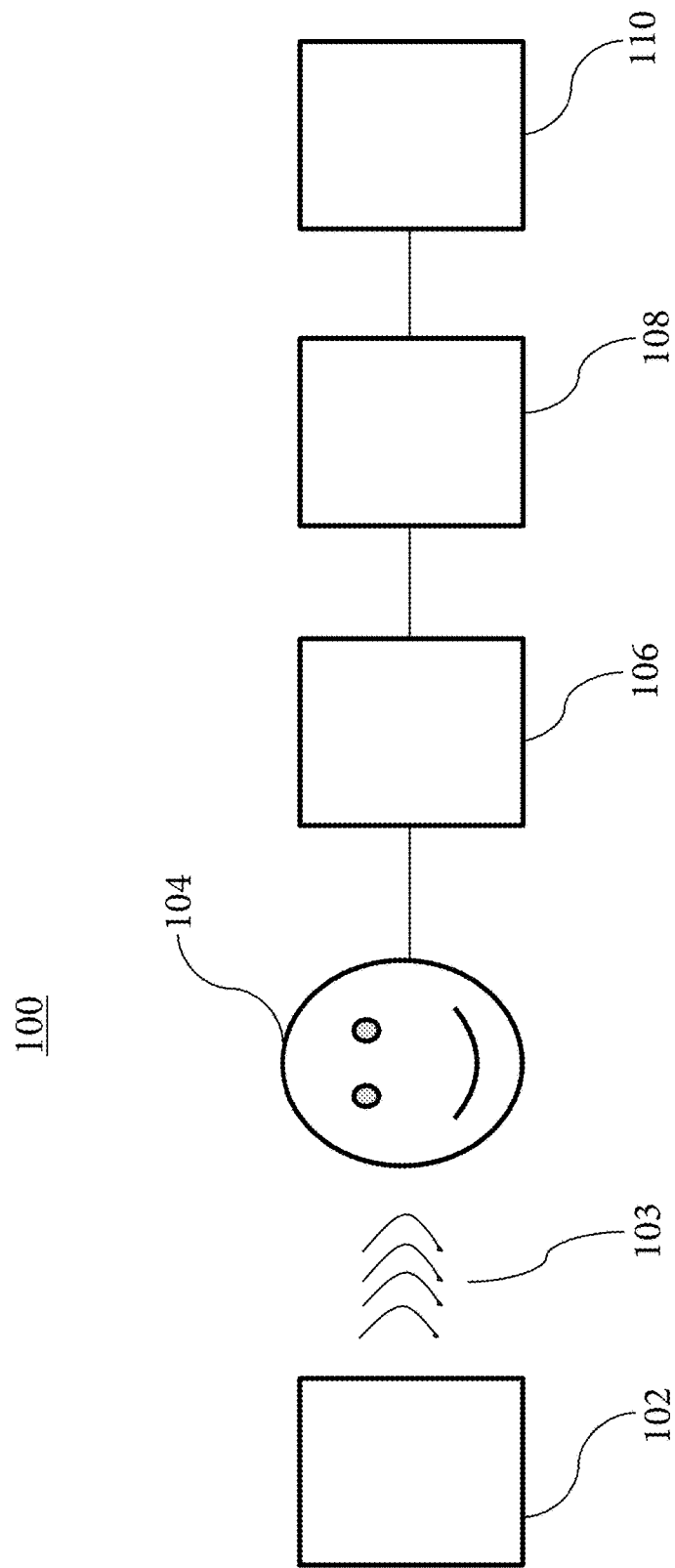

FIG. 13 is a block diagram of an exemplary embodiment of a system for evaluting evoked potentials in accordance with the present invention.

5. DETAILED DESCRIPTION OF THE INVENTION

Reference will now be made in detail to the exemplary embodiments of the present invention, which are illustrated in the accompanying drawings. The system and corresponding method of the present invention will be described in conjunction with the detailed description of the system.

The methods and systems presented herein may be used for profiling auditory evoked potentials in brain electrical activity which apply steady state response concepts to analysis of longer latency responses reflective of activity of brain regions beyond the brainstem, up to an including the cortex.

With reference to FIG. 13, an exemplary embodiment of a system 100 for evaluating evoked potentials in brain electrical activity using auditory steady state profiling is provided. The system 100 includes an auditory signal generator 102 configured to administer an auditory stimulus 103 to a subject 104 at a predetermined frequency to generate an auditory evoked potential in the subject 104 indicative of cortical activity of the brain. The system 100 further includes a sensor 106 for measuring amplitudes of the auditory evoked potential. The system 100 further includes a processor 108 coupled to the sensor 106 and configured to receive the measured amplitudes of the auditory evoked potential therefrom. The processor 108 can be configured to identify a plurality of spectral components of the auditory evoked potential and calculate a harmonic sum of the plurality of spectral components to determine an overall amplitude of the auditory evoked potential. The system 100 can further include an output 110 operably coupled to the processor and can be configured to display the overall amplitude of the auditory evoked potential and the plurality of spectral components.

Figure 1:
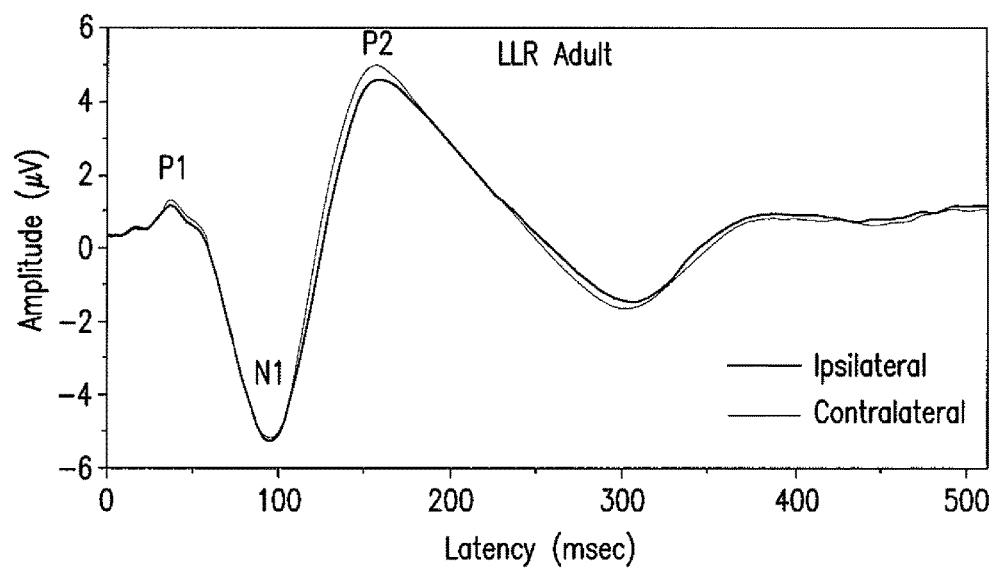
FIG. 1 is a graphical representation of an conventional auditory evoked potential using transient stimulus.

Conventional auditory evoked potential techniques employ transient stimuli which evoke a multi-phasic transient response that does not reflect or relate directly to the stimulus spectrum. An example of an auditory evoked potential obtained via the traditional approach is illustrated in FIG. 1 in which a brief 1 kHz sinusoidal pulse was administered at less than 1/s at 70 db SPL, which is a moderate intensity level representative of conversational levels of speech. The wave form illustrated includes a first peak (P1), a first minimum (N1), and a second peak (P2), which is indicative of a neurologically intact adult. Such conventional transient techniques derive from time ensemble averaging of multiple stimulus presentations, which are effectively overlaid in time to extract the desired response signal(s) from the noise background. Typically, the signal extracted from the noise background (also referred to herein as noise floor) can range from about 10 micovolts, down to fractional microvolts for the shortest-latency responses. In effect, the response potential is treated as a single event under this transient technique such that for each stimulus administered to a subject there is a corresponding and discrete response evoked. However, in conventional practice the response is estimated via long-term averaging over all stimulus repetitions.

As discussed above, the transient auditory evoked potential reflects essentially the impulse response of the system and is not directly representative of the spectrum of the input signal. Further, the analysis of the transient auditory evoked potential suffers from "picking" and interpreting peaks of the response waveform. This can be problematic due to the inherent variability of the waveform, e.g., across and even within subjects, or due to residual noise. These variations or fluctuations in the waveform of transient responses can be further compounded by factors of sleep, maturation level of the subject, and/or sensory deficits of the subjects. This leads to difficulty and uncertainty in transient analysis and interpretation as changes are not easily quantified and/or isolated in an unambiguous manner. This is particularly problematic in attempting to separate the influence of background electroencephalogram and other components of the noise floor.

Figure 2:
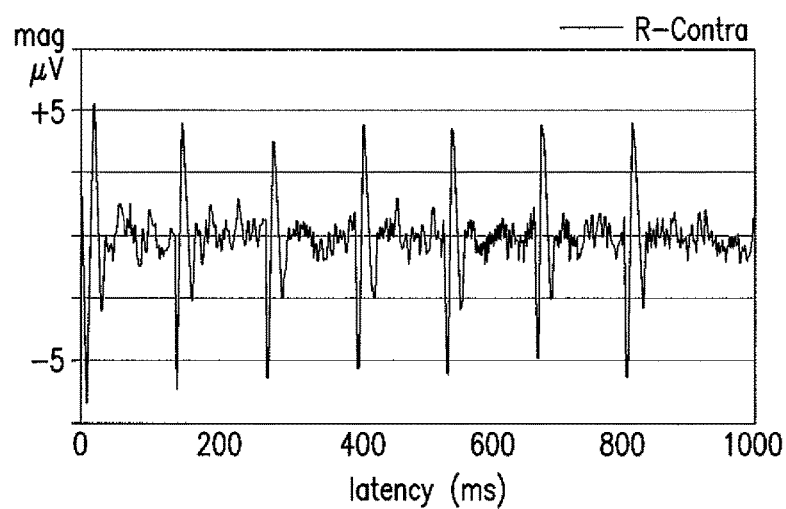
FIG. 2 is a graphical representation of auditory evoked potentials generated by repeated stimulus over a predetermined window to define a quasi-steady-state response.

Therefore, and in accordance with an aspect of the present invention, a steady-state response approach is employed in analyzing auditory evoked potentials in order to take advantage of the inherently deterministic aspects of this technique. As illustrated in FIG. 2, repeated stimuli are administered within an analysis window having a latency of a 10,000 milliseconds, in which the P1-N1-P2, i.e. the vertex potential, complexes are repeated to permit a quasi-steady-state response and high resolution spectral analysis, while still allowing for time ensemble averaging. This technique is applicable even for evoked potentials corresponding to the auditory long-latency response which can be evoked at a stimulus repetition rate (also referred to as a modulation frequency (Fm)) to below 1 Hz. Further, and in accordance with the present invention, the steady-state response technique eliminates the disadvantages of time-domain peak-picking, and allows for a complete spectral analysis. As discussed herein the spectral analysis of the present invention can include measurement of overall response power, detailed harmonic structure analysis, magnitude-vs-phase comparison, and other analyses of components of the evoked response, as so desired.

5.1 Methods 5.1.1 Subjects

The adult cohort comprised twenty-five subjects, 18 to 35 years of age, and the pediatric cohort comprised twelve children 6-9 years of age. In an effort to minimize gender effects, the subjects were all females. No subject had a personal history of otological or neurological disorders. Each subject demonstrated normal middle ear function in both ears as defined by unremarkable otoscopic and tympanometric results (peak pressure within ±100 daPa). All subjects had normal hearing sensitivity in both ears, thereby corroborating the assumption of an overall intact auditory nervous system. Hearing sensitivity was measured using the modified Hughson-Westlake procedure, as known in the art. Pure-tone thresholds were determined to within 5 dB, per standard clinical procedure (ANSI, 1996). Hearing with normal limits was defined more rigorously than by clinical practice, namely by thresholds of 15 dB HL or better for pure-tone octave frequencies between 0.25 and 8 kHz. In addition, all subjects demonstrated the main component waves of transient auditory evoked potential response measurements in the three major latency groups.

5.1.2 Stimuli

The stimuli for transient and steady-state recordings were generated using Intelligent Hearing Systems (Miami, Fla.) SmartASSR evoked potential (EP) software. The routinely distributed auditory steady-state response software provides stimulus control and analysis for testing using at repetition rates of 40 Hz and above. To permit testing lower rates, e.g., 20 Hz and below, alternative versions of control modules were provided to set the repetition rate and corresponding response windowing, thereby over-riding initialization. The use of manufacturer-supplied modifications assured operation without significant degradation of the performance of the instrumentation and/or substantive deviations from the FDA approved use of this instrumentation. Other adaptations needed to accomplish the specific aims of the study were accomplished via SmartEP utilities and external software used to analyze ASCII downloads of the data. Similarly, conventional transient response testing was accomplished using the standard SmartEP software (i.e. implemented on the same instrumentation platform). Indeed, the parameters chosen for the lowest stimulus repetition rate were chosen to provide essentially overlapping paradigms, yielding essentially identical time-domain responses via either paradigm.

The stimuli for the auditory brainstem response (ABR), middle latency response (MLR) and long-latency response (LLR) all were 1 kHz tone bursts (TBs). This stimulus was chosen for purposes of a uniform comparison across latency ranges, although adjusted by other parameters (e.g., rise-fall time and duration) to be a mutually effective stimulus across repetition rates. Because the transient auditory evoked response literature provides limited guidance for systematically choosing TB parameters over the breadth of range used in this study, a rule-based approach was sought by which to systematically vary rise and fall, and overall duration as a function of repetition rate. The envelope parameters were adjusted so as to be increased by 1.414× with each decrease in repetition rate. The envelope itself was the extended cosine, to ensure an adequately abrupt on-set (for excellent neural synchrony) while, again, maintaining reasonable frequency specificity. Repeated TBs was first used for the 40-Hz steady-state responses ASSR (Galambos et al., 1981). Repetition rates were at octave or nearly octave intervals from 80 Hz down. The envelope parameters for both transient auditory evoked potentials (AEP) and auditory steady-state responses (ASSR) are outlined in Table 1.

TABLE 1

Envelope parameters for transient auditory evoked potentials (AEP) and auditory steady-state responses (ASSR)

|      | Rate  | Rise/Fall | Duration |
|------|-------|-----------|----------|
| ABR  | 20    | 1         | 4        |
| MLR  | 10    | 2.8       | 11       |
| LLR  | 0.75  | 11        | 45       |
| ASSR | 80    | 1         | 4        |
|      | 40    | 1.4       | 5.6      |
|      | 20    | 2         | 8        |
|      | 10    | 2.8       | 11       |
|      | 5     | 4         | 16       |
|      | 2.5   | 5.6       | 23       |
|      | 1.25  | 8         | 32       |
|      | 0.75  | 11        | 45       |

5.1.3 Recordings

Silver-silver chloride electrodes were affixed at vertex (shared across channels, non-inverting input), ipsilateral and contralateral mastoid (inverting inputs) and nasion (ground of the recording amplifiers). Inter-electrode impedances of less than 5 kilohms at 30 Hz (Grass Instruments EC2) were achieved in all subjects. The same two-channel electrode montage and type of recording electrodes were used for both transient and steady-state AEP testing. For the auditory steady-state response, an entire sweep (1024 points) was rejected if it contained any potential with voltage amplitudes greater than ±50 microvolts within 50 millisecond window. For repetition rates of 40 and 80 Hz, the evoked response test system used an analog-to-digital conversation rate of 20 kHz, which was down-sampled to 1 kHz for a final spectral resolution of 0.9765 Hz. For lower repetition rates, progressively lower sampling rates (SR) and longer acquisition windows (AW) were required as repetition rate was decreased below 40 Hz. Time-ensemble averaging was incorporated to enhance the signal-to-noise prior to spectrum analysis. The maximum number of sweeps averaged was proportionally varied such that the total acquisition time for each repetition rate was approximately four minutes. Separate parameters chosen to enable the recordings of transient AEPs and ASSRs are outlined in Table 2.

TABLE 2

Recording parameters for transient auditory evoked potentials (AEP) and auditory steady-state responses (ASSR)

|      | Sampling | Acquisition | Number of Gain | B-pass | Sweeps |
|------|----------|-------------|----------------|--------|--------|
| ABR  | —        | 11/ms       |        100     | 100-3000 | 4096 |
| MLR  | —        | 100         |        100     | 10-1500  | 2048 |
| LLR  | —        | 500         |         50     | 0.4-30   | 512  |
| ASSR | 1000     | 1.024/s     |   80   100     | 100-3000 | 160  |
|      | 1000     | 1.024       |   40   100     | 100-3000 | 160  |
|      | 800      | 1.28        |   22   100     | 0.4-100  | 160  |
|      | 400      | 2.56        |   22   100     | 0.4-100  | 80   |
|      | 200      | 5.12        |   22   100     | 0.4-100  | 40   |
|      | 100      | 10.24       |   13   100     | 0.4-100  | 20   |
|      | 100      | 10.24       |   10   100     | 0.4-100  | 20   |
|      | 100      | 10.24       |    7   100     | 0.4-100  | 20   |

5.1.4 Procedure

Subjects were tested in 2 recording sessions (approximately 1.5 hours each), on average 12 days apart. Pure-tone behavioral threshold and auditory steady-state response testing was completed with subjects comfortably semi-reclined in a double-walled sound treated booth. Steady-state responses were recorded with the subject alert and awake. In order to limit recording sessions to a reasonable time period, only the right ear from each subject was tested. This constraint was imposed, as well, to avoid the removal or replacement of the transducer within recording sessions, for optimal signal stability within and across tests. Pure-tone behavioral thresholds for octave frequencies between 0.25-8 kHz and a screening ABR, MLR and LLR were obtained in the initial recording session. Auditory steady-state responses were obtained in the second recording session at the eight repetition rates, as well as one within-test session recording. Additionally, and in order to avoid a false impression of a reproducible peak component, two no-stimulus control trials were carried out to serve as a baseline from which to judge the amplitude of the noise in the auditory steady-state response stimulus evoked response.

Subjects were seated in a lighted sound treated room and were instructed to remain awake and alert during LLR and MLR testing. To assure alertness, the subject's were required to count the number of tones during each recording. During recording, electroencephalography (EEG) and eye tracking was monitored continuously to ensure no hallmarks of drowsiness or sleep were observed during testing (e.g., decrease or disappearance in electrical activity recorded from the scalp surface, very slow eye movement or cease of eye blinking). During ABR testing the light in the sound treated room was turned off and all subjects were encouraged to sleep. The insert earphone was kept in place without removal or repositioning throughout the recording session.

5.2 Spectral Analysis for Quasi-Steady-State

Conventional approaches to auditory evoked responses focus on the spectral power at the fundamental frequency, which is the lowest frequency in a harmonic series, in order to analyze the amplitudes of the responses (defined below). However, and in accordance with the present invention, the power at the fundamental frequency accurately account for the power in the overall spectrum of all responses. This is particularly relevant at the lowest repetition rate, where the fundamental can be difficult to detect and/or is not the dominant spectral component. Accordingly, the present invention provides an overall amplitude measure of the response. A conventional measure from acoustics is that of percent total harmonic distortion (THD). For instance, THD is specified in the performance analysis of stereo hi-fidelity amplifiers. This measure is calculated as follows:

$$THD = 100 \times \sqrt{\frac{p2^2 + p3^2 + p4^2 \ldots}{p1^2 + p2^2 + p3^2 \ldots}} \quad [\text{Eq. 1}]$$

where $p^1$, $p^2$, $p^3$ ... are the observed sound pressures or voltages observed at frequencies $F_1$, $F_2$, $F_3$, etc., namely the fundamental frequency (F1) and its harmonics, wherein subscript 1 is the fundamental frequency and successive integers$\geq 2$ denote the harmonics. However, in the present invention, an alternative equation was derived utilizing the term appearing in the denominator of Eq. 1, i.e. the sum of the voltages squared, including both the fundamental and all measureable harmonics. Thus, Eq. 1 was modified to define the measure used, dubbed herein as the "harmonic sum" (HS) and computed as follows:

$$HS = \sqrt{p1^2 + p2^2 + p3^2 \ldots} \quad [\text{Eq. 2}]$$

For spectral analyses and to compute the HS from the data generated by the software employed herein, two spectral analyses were made: the first was that of the 'response' estimate which was the average of the rarefaction and condensation sweeps of the two buffers (apropos the "split" or double-buffering employed in the signal acquisition protocol of the test system employed); the second was that of the "noise" estimated, computed as the difference between the two buffers. Knowing the integer values from the power spectrum analysis, representing the voltage squared of the amplitudes, the HS can be computed by taking simply the square root of the sum of these values for the spectral components identified to significantly exceed the noise floor, as described in further detail below.

In accordance with an aspect of the present invention, and in order to analyze the individual responses, the total response at each repetition rate is examined for spectral components that are identified to be integer multiples of the fundamental frequency (F1). Contralateral recordings are analyzed for responses at repetition rates 40 Hz, while ipsilateral recordings are analyzed for responses at 80 Hz, in order to investigate the crossed ascending auditory pathway and levels of response generation (as discussed in above). In deference to inherent limits of frequency resolution via digital analyses (e.g., binary rounding), the frequency component was scored and its amplitude taken as the peak falling±5% of the target frequency. The estimated background noise spectrum was then superimposed on the response spectrum to identify the components at the fundamental frequency (F1) and its harmonics, in order to determine which components were greater than the noise floor, i.e., having a signal-to-noise greater than 0. For purposes of presenting and characterizing the grand averaged response and noise spectra, as discussed in more detail below, each spectrum was normalized relative to the maximum power at each repetition rate. Additionally, and as presented herein, graphical plots with the response/amplitude spectra and noise spectra superimposed permit direct comparison, facilitate comparisons across components of differing harmonic number, and simplify comparisons across repetition rate.

Figure 3:
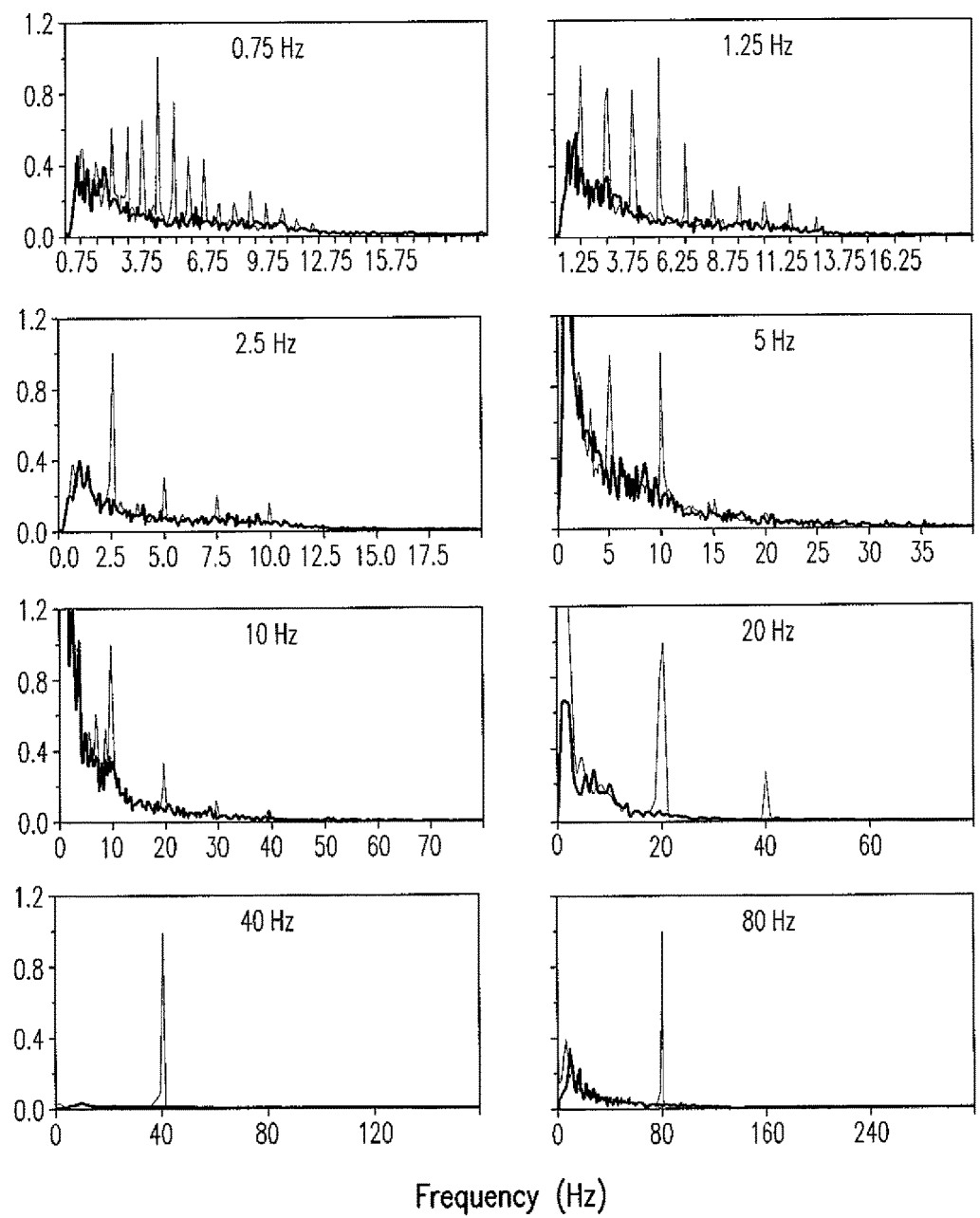
FIG. 3 is a series of graphical representations of grand averages of the auditory steady-state response power spectra at each repetition rate.

For purpose of illustration and explanation, grand averages of the auditory steady-state response power (or amplitude) spectra at each repetition rate are displayed in FIG. 3. The total response and the estimated background noise are superimposed in each of the representative plots, with the noise depicted by the line of greater weight. At 0.75 and 1.25 Hz, the averaged steady-state response is represented by a series of spectral components at integer multiples of the fundamental frequency (F1). Of these spectral components, the greatest amount of power occurs at several harmonics of the fundamental frequency. For example, at 0.75 Hz, the maximal amplitude was at the sixth harmonic (4.5 Hz), while at 1.25 Hz, the greatest power moved to the fourth harmonic (5 Hz), that is, slightly closer to the fundamental frequency (F1) of 1.25 Hz. At 2.5 Hz, 5 Hz and 10 Hz, the averaged response is represented by fewer spectral harmonic components at or above the fundamental frequency (F1). Of these harmonic components, the greatest amount of power occurred either at the fundamental frequency or primarily the second harmonic. At 20, 40 and 80 Hz, the averaged steady-state response was represented by only a small number of spectral components at integer multiples of the fundamental frequency. Of these spectral components, the greatest amount of power occurred at the fundamental, with diminishingly small powers at the second and third harmonics by 40 Hz.

Figure 4:
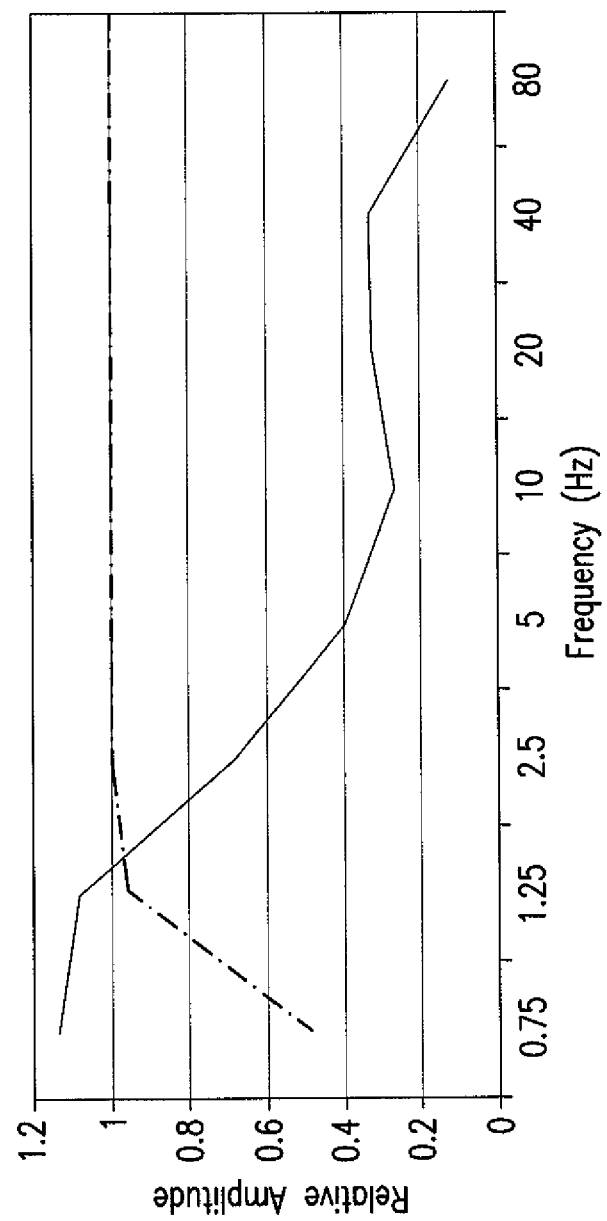
FIG. 4 is a graphical representation comparing the response profile obtained by the steady-state response technique of the present invention to the conventional transient analysis.

FIG. 4 illustrates the significance of the harmonic sum of the response in accordance with the present invention. Particularly, FIG. 4 depicts that the overall amplitude of the response decreased as repetition rate increased from 0.75 to 80 Hz. To demonstrate the use of harmonic structure in response measurement, the harmonic sum of the response and the analysis based on the fundamental frequency have been superimposed in FIG. 4. The analysis based on the harmonic sum (shown in solid line) revealed that amplitude was largest at 0.75 Hz and smallest at 80 Hz, while the analysis based on the fundamental frequency alone (shown in broken line) revealed that amplitude remained largest at 2.5 through 80 Hz and was smallest at 0.75 Hz. Accordingly, the detailed analysis of the various spectral components of the evoked response provided by the harmonic sum and steady-state response technique of the present invention allows for a more accurate and informative presentation of the evoked response.

5.3 Examples and Discussion

As discussed above, the steady-state response technique of the present invention allows for a spectral analysis of the evoked response, particularly for long-latency responses. In the example illustrated in FIGS. 5A-B, the modulation frequency employed was low enough to also produce essentially the same long-latency response as recorded via conventional transient techniques (as illustrated in FIG. 1) and indeed demonstrate quasi-discrete spectra with components at the modulation frequency (Fm) and its harmonics, as described above. FIG. 5A depicts a steady-state response simulated from long-latency response data obtained by duplicating the epoch to emulate repeated stimuli (also referred to as "response train") within the analysis window. Comparisons are provided between the spectrum of an individual epoch (also referred to as "single response") versus the quasi-steady-state response ("response train"). The repeated stimuli ("response train") is shown to approximate a discrete spectrum and the spectral envelope follows that of the individual (transient) response. Frequency and amplitude scales are relative in this representation. Similarly, FIG. 5B depicts a comparison of the simulated steady-state response using actual long-latency response data (referred to as "real" in the plot) versus a long-latency-like waveform which is synthesized using haversines of progressively longer period from P1-P2 (referred to as "synthesized" in the plot). The overall spectral results depicted demonstrate spectral features that are valid (i.e. rather than noise or other artifact). For long-latency auditory evoked potentials, wherein duty-cycle of the response is quite low, the response spectrum is inherently complex and may not necessarily show the highest power to occur at the fundamental frequency (Fm), as discussed with reference to FIG. 3 above.

FIG. 6 provides the grand average of the amplitude spectrum of the evoked response at a repetition (or frequency modulation), of 0.75 Hz. Particularly, FIG. 6 illustrates the relative amplitude spectrum from steady-state response stimulus in accordance with the present invention, which is normalized to largest spectral peak. Further, FIG. 6 depicts both the evoked potential (also referred to as "Response" in the plot) as well as the estimated noise floor (also referred to as "Est. Noise" in the plot) which is derived by taking the difference between the two-buffers of the dual-buffered response acquisition process, as described above. As illustrated, the noise has a maximum amplitude, which is approximately equal to the response, at about 0.75 Hz.

In accordance with an aspect of the present invention, the observed grand average spectrum of the steady-state response using the approach described herein achieves the level of predictability sought of the deterministic approach to response-stimulus analysis. Further, the approach disclosed herein is particularly advantageous as modulation frequency is lowered, which results in the spectral power being less concentrated at the modulation frequency, and more dispersed about the harmonic structure of the response, as described above. Additionally, the effective rise-time of the stimulus envelope at lower modulation frequencies can prove too long to robustly stimulate auditory evoked potentials utilizing conventional techniques. Thus the steady-state approach of the present invention is applicable to a broad latency range of auditory evoked potentials, particularly the obligatory sensory evoked potentials defined as long, middle, and short latency responses.

In accordance with another aspect of the invention, a comparison between states of awake and light sleep (dozing) in the same subjects was conducted. Similar to the previously described methods, stimuli were repeated tone bursts at 1 kHz. Spectral analyses of the steady-state responses demonstrated responses that remained relatively robust for all repetition rates. Results for Fm=0.75 Hz are shown in FIGS. 7A-B. As illustrated, the steady-state response/long-latency response exhibits sensitivity to level of arousal, yet is robust in dozing subjects. It is difficult, if even possible, to examine this effect via traditional transient response due to the uncertainty in distinguishing the response versus residual noise. Consequently, it errors can occur in attempting to unambiguously quantify the auditory evoked potential. As discussed above regarding the interpretive aspect of conventional time analysis of the response, both background electroencephalogram and the response are sleep-level dependent. Therefore, it is advantageous to have a means to objectively separate response and background noise components, as provided by the present invention.

FIG. 7A represents the grand average amplitude spectrum of responses in which the subjects are awake, while FIG. 7B depicts the amplitude spectrum of subjects under light-sleep (dozing) conditions. While sleep analysis was not performed, all subjects reported dozing off during this phase of testing, in contrast to the awake phase, wherein they were watching a movie (absent any audio that may interfere with the stimulus). For sake of comparison, spectral power has been normalized to the awake relative amplitude scale. As illustrated, the spectral envelope varies between the two conditions. For example, the maximum amplitude under light-sleep conditions is more than double the value of the maximum amplitude under awake conditions. Furthermore, although a similar center of gravity is depicted between both conditions, differences in the noise floor are exhibited in the two conditions. For example, the estimated noise floor under light-sleep conditions exhibits an amplitude of approximately 0.6 at a frequency of 7.5 Hz and 9.75 Hz, whereas the amplitude under awake conditions remains substantially constant from a frequency of approximately 6 Hz. Unlike the conventional transient response, the effects of sleep response and background noise can be readily separated in the steady-state response of the present invention.

In accordance with another aspect of the invention, the steady-state response disclosed herein was applied to a cohort of children wherein the sample size was 12, and the ages of the subjects ranged from 6-9 years of age. The results of which are illustrated in FIGS. 8A-B show equal efficacy for steady-state response assessment of the long-latency responses. Particularly, FIG. 8A depicts the grand average transient response, while FIG. 8B depicts the steady-state response amplitude spectrum of the present invention. Upon comparison of the transient responses of pediatric subjects (FIG. 8A) to adult subjects (FIG. 2) it is evident that although the P1 components share a common behavior, the pediatric long-latency response shows immaturity of the N1-P2 complex as compared to adults. Consequently, this discrepancy can further confound correct wave interpretation in traditional transient techniques. For purposes of comparison, spectral power is normalized to adult sample average. Upon comparison of the steady-state responses of pediatric subjects (FIG. 8B) to adult subjects (FIG. 6) it is evident that there are fewer spectral peaks, a lower center of gravity of the spectral power, and the nearly doubling of the amplitude scale in the pediatric response.

FIGS. 9-12 illustrate findings of profiling relative spectral power across modulation frequency for a number of comparisons. It is to be understood that the applications illustrated herein are for explanation and illustration purposes, and do not encompass or limit the applications of the present invention. The results illustrated are from the grand-average spectra for the respective subject groups or conditions, wherein a single magnitude value per modulation frequency (Fm) was sought to represent the overall response. This value was computed for the total number of spectral components that were greater than the noise estimate at all multiples (i.e. harmonics, nFm) of the modulation frequency, starting with the frequency module itself. This value, referred to as the overall spectral sum, is computed based on the total harmonic distortion, as discussed herein. This approach is based on the observation that limiting analysis to the modulation frequency Fm would grossly under-estimate the overall response magnitude for 20 Hz and below, and dramatically so below 5 Hz.

FIG. 9 illustrates a further comparison of the pediatric and adult steady-state response, wherein the pediatric response is substantially larger than in adults at low modulation frequencies. However, this trend is reversed at modulation frequencies above 20 Hz.

FIG. 10 illustrates a comparison of transient response data for different stimulus repetition rates. The pediatric response depicted in FIG. 10, which reflects the traditional transient approach, exhibits lower amplitude than that of the adults. This is in contrast to the findings illustrated in FIG. 9, which illustrate pediatric vs. adult results obtained via the steady-state response approach. However, an explanation for this discrepancy is that the steady-state response of the present invention captures the entire response power, and as discussed above, and not merely the N1-P2 magnitude, which is the typical amplitude measurement of the transient response technique. Further, it is noteworthy that the subject sample size for the transient data was 12 whereas the subject sample size for the steady-state response data was 25.

FIG. 11 illustrates a comparison between the pediatric profile and sub-groups, or "split-half", profiles from the adult sample. To conduct this measurement, the subjects were randomly assigned to two sub-groups. Standard-error bars are included for the various profiles and represent a greater variability than the difference between the two split-half groups. This relatively large standard-error of the pediatric profile can be attributed to, among other things, the maturational variance even within the 3-year age constraints of the pediatric group, i.e. ages 6-9 years (with a sample size of 12).

FIG. 12 illustrates the effects of light sleep on the profile. As expected for the spectra, the evoked response under sleep condition is more robust with a greater amplitude, however this enhancement diminishes at 5 Hz-10 Hz. The 40-Hz auditory steady-state response is known to be somewhat vulnerable to sleep, as appears to be the 20-Hz response. The auditory steady-state response at 80 Hz and above, which is comparable to the auditory brain-stem response to a brief transient signal, is shown to be independent of the level of arousal.

Accordingly, and as discussed above, the steady-state response technique disclosed herein allows for quantitative analysis, for example, identifying spectral peaks above the noise floor, and thereby reducing possible confounds that depend upon developmentally related differences in the stimulus-related response itself, as well as any background noise. This is particularly advantageous for equating the traditional peaks of the time-domain response, over a decreasing age of the examinee. While the time-domain components of a response are of interest with respect to their individual generators, the steady-state approach of the present invention provides a means by which to gain additional information and/or measurements in a format that can be consistently implemented and/or more attractive for certain applications, such as to profile the responses over broad ranges of stimulus repetition rates. Particularly, the spectra of responses at the lower stimulation rates are necessarily complex, yet valid estimates of the response's magnitude. By employing the steady-state response approach, the spectra are essentially discrete and thus readily accessible to further quantitative analyses, e.g. starting with overall spectral power as expressed by the harmonic sum.

Further, the present invention allows for the identification and evaluation of the function of spectral power of the response as compared to the repetition rate. This includes analyzing the response magnitude across traditional latency domains. This is an improvement over traditional transient techniques which do not adequately provide or allow for this function due to the problem of wave identification/interpretation. Considering the neuroanatomical bases of the behavior of the steady-state responses over modulation frequency, as discussed herein, this profile can provide a useful technique for a broad variety of neurological and/or audiological interests.

For example, in particular non-limiting embodiments, the present invention provides for a method of evaluating central nervous system function in a test subject, comprising:

(i) administering an auditory stimulus to the test subject over a range of predetermined frequencies, the auditory stimulus generating an electrical activity in the test subject;

(ii) synchronizing the electrical activity in the test subject with the auditory stimulus to define an auditory evoked potential;

(iii) identifying a plurality of spectral components of the auditory evoked potential of the test subject;

(iv) calculating the harmonic sum of the plurality of spectral components of the test subject;

(v) determining the overall amplitude of the auditory evoked potential in the test subject, wherein the overall amplitude includes the plurality of spectral components; and (vi) comparing the overall amplitude of the auditory evoked potential in the test subject with the overall amplitude of the auditory evoked potential in a control subject, where a difference between overall amplitude of the auditory evoked potential in the test subject relative to the control subject indicates that there is a defect in the central nervous system function of the test subject. In some embodiments, a decrease in the amplitude of the auditory evoked potential in the test subject relative to the control subject will reveal that the defect can be the result of a developmental disorder, a degenerative condition, or an injury that may be traumatic, metabolic, ischemic or toxic.

Accordingly, the steady-state response technique described herein thus permits profiling maturation and state effects in a manner that avoids issues of wave interpretation and minimizes complications of concomitant differences in background noise. Furthermore, this technique is readily amenable to objective analyses and data recordation including computer scoring or tracking of responses. Additionally the present invention can be employed in a myriad of diverse applications including brain-damaged subjects (e.g. head injury, stroke, etc.); electric response audiometry (both threshold prediction and "hearing screening"), namely to work with the longer-latency (more cortical-ward generated) potentials which may be indicative of auditory function closer to the level of conscious behavior. Furthermore, while the present invention relates to overall response independent of conventional wave (peak) identification, individual spectral features are reasonably expected to be associated with conventionally identified peaks (e.g. P1 of the long-latency response P1-N1-P2 complex), if not isolatable using spectral analysis with repetition rate(s) that may facilitate the elicitation of targeted waves.

While the present invention is described herein in terms of certain preferred embodiments and/or applications, those skilled in the art will recognize that various modifications and improvements may be made to the present invention without departing from the scope thereof. Moreover, although individual features of one embodiment of the present invention may be discussed herein or shown in the drawings of the one embodiment and not in other embodiments, it should be apparent that individual features of one embodiment may be combined with one or more features of another embodiment or features from a plurality of embodiments.

In addition to the specific embodiments claimed below, the present invention is also directed to other embodiments having any other possible combination of the dependent features claimed below and those disclosed above. As such, the particular features presented in the dependent claims and disclosed above can be combined with each other in other manners within the scope of the present invention such that the present invention should be recognized as also specifically directed to other embodiments having any other possible combinations.

Thus, the foregoing description of specific embodiments of the disclosed subject matter has been presented for purposes of illustration and description. It is not intended to be exhaustive or to limit the disclosed subject matter to those embodiments disclosed. It will be apparent to those skilled in the art that various modifications and variations can be made in the method and system of the present invention without departing from the spirit or scope of the present invention. Thus, it is intended that the present invention include modifications and variations that are within the scope of the appended claims and their equivalents.

What is claimed is:

1. A method of evaluating auditory steady state responses comprising:

administering, by an auditory signal generator, an auditory stimulus to a subject at a predetermined frequency to generate an electrical activity in the subject;

synchronizing the electrical activity in the subject with the auditory stimulus to define an auditory evoked potential;

measuring, by a sensor, amplitudes of the auditory evoked potential;

identifying, by a processor coupled to the sensor and configured to receive the measured amplitudes of the auditory evoked potential therefrom, a plurality of spectral components of the auditory evoked potential, the plurality of spectral components comprising a fundamental frequency and one or more harmonic frequencies; and calculating, by the processor, a harmonic sum of the plurality of spectral components to determine an overall amplitude of the auditory evoked potential, the harmonic sum comprising a square root of a sum of the amplitudes squared of the auditory evoked potential at the fundamental frequency and the one or more harmonic frequencies.

2. The method of claim 1, wherein the overall amplitude includes a fundamental frequency of the stimulus.

3. The method of claim 1, wherein the identified one or more harmonic frequencies each have an amplitude greater than an estimated noise value.

4. The method of claim 1, wherein the predetermined frequency is greater than 0 Hz and less than 10 Hz.

5. The method of claim 1, wherein the predetermined frequency is greater than 0 Hz and less than 1 Hz.

6. The method of claim 1, wherein the predetermined frequency comprises a plurality of predetermined frequencies progressively decreasing from 80 Hz to 0.75 Hz, and the method is performed for each of the plurality of predetermined frequencies.

7. The method of claim 1, wherein the stimulus is administered at 70 decibels.

8. The method of claim 1, wherein the stimulus is a sinusoidal pulse.

9. The method of claim 1, wherein the stimulus is administered to the subject while the subject is awake.

10. The method of claim 1, wherein the stimulus is administered to the subject while the subject is in a state of light sleep.

11. The method of claim 1, wherein the subject is an adult of at least 18 years of age.

12. The method of claim 1, wherein the subject is a child at least 6 years of age and no more than 9 years of age.

13. The method of claim 1, wherein the auditory evoked potential in the subject reflects cortical activity of the brain.

14. A system for evaluating evoked potentials in brain electrical activity using auditory steady state profiling comprising:

an auditory signal generator configured to administer an auditory stimulus to a subject at a predetermined frequency to generate an auditory evoked potential in the subject indicative of cortical activity of the brain;

a sensor for measuring amplitudes of the auditory evoked potential;

a processor coupled to the sensor and configured to receive the measured amplitudes of the auditory evoked potential therefrom, the processor configured to:

identify a plurality of spectral components of the auditory evoked potential, the plurality of spectral components comprising a fundamental frequency and one or more harmonic frequencies, and calculate a harmonic sum of the plurality of spectral components to determine an overall amplitude of the auditory evoked potential, the harmonic sum comprising a square root of a sum of the amplitudes squared of the auditory evoked potential at the fundamental frequency and the one or more harmonic frequencies; and an output operably coupled to the processor and configured to display the overall amplitude of the auditory evoked potential.

15. The system of claim 14, wherein the processor is further configured to identify the one or more harmonic frequencies each having an amplitude greater than an estimated noise value.

16. The system of claim 14, wherein the auditory signal generator is further configured to administer the auditory stimulus at the predetermined frequency, wherein the predetermined frequency is greater than 0 Hz and less than 10 Hz.

17. The system of claim 14, wherein the auditory signal generator is further configured to administer the auditory stimulus, wherein the stimulus comprises a sinusoidal pulse.

18. The method of claim 1, further comprising displaying the overall amplitude of the auditory evoked potential.

* * * * *

UNITED STATES PATENT AND TRADEMARK OFFICE
CERTIFICATE OF CORRECTION

PATENT NO. : 9,662,035 B2
APPLICATION NO. : 13/307212
DATED : May 30, 2017
INVENTOR(S) : John David Durrant et al.

It is certified that error appears in the above-identified patent and that said Letters Patent is hereby corrected as shown below:

On the Title Page

Please add the following in section Related U.S. Application Data:
-- (60) Provisional application No. 61/183,826, filed on Jun. 3, 2009. --

Also, please update "(63) Continuation of application No. PCT/US2010/037312, filed on Jun. 10, 2010" should read:
-- (63) Continuation of application No. PCT/US2010/037312, filed on Jun. 3, 2010. --

Signed and Sealed this
Twelfth Day of September, 2017

Joseph Matal
*Performing the Functions and Duties of the*
*Under Secretary of Commerce for Intellectual Property and*
*Director of the United States Patent and Trademark Office*